United States Patent
Zadrozny et al.

(10) Patent No.: US 7,143,044 B2
(45) Date of Patent: Nov. 28, 2006

(54) TRANSLATOR FOR INFANTS AND TODDLERS

(75) Inventors: Wlodek W. Zadrozny, Tarrytown, NY (US); Dimitri Kanevsky, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 927 days.

(21) Appl. No.: 09/751,504

(22) Filed: Dec. 29, 2000

(65) Prior Publication Data

US 2002/0084902 A1 Jul. 4, 2002

(51) Int. Cl.
*G10L 21/00* (2006.01)

(52) U.S. Cl. .................. 704/275; 704/270; 704/277
(58) Field of Classification Search ............... 704/270, 704/275, 276, 277
See application file for complete search history.

(56) References Cited

U.S. PATENT DOCUMENTS

| | | | | |
|---|---|---|---|---|
| 5,526,465 | A | * | 6/1996 | Carey et al. ............. 704/250 |
| 5,596,994 | A | * | 1/1997 | Bro ........................ 600/545 |
| 5,722,418 | A | * | 3/1998 | Bro ........................ 600/545 |
| 5,913,310 | A | * | 6/1999 | Brown .................... 128/897 |
| 5,970,448 | A | * | 10/1999 | Goldhor et al. ......... 704/235 |
| 5,983,190 | A | * | 11/1999 | Trower et al. ........... 704/276 |
| 6,006,175 | A | * | 12/1999 | Holzrichter ............. 704/208 |
| 6,048,209 | A | * | 4/2000 | Bailey .................... 434/267 |
| 6,186,145 | B1 | * | 2/2001 | Brown .................... 128/897 |
| 6,292,830 | B1 | * | 9/2001 | Taylor et al. ............ 709/224 |
| 6,334,778 | B1 | * | 1/2002 | Brown .................... 434/258 |
| 6,404,438 | B1 | * | 6/2002 | Hatlelid et al. ......... 345/473 |
| 6,421,453 | B1 | * | 7/2002 | Kanevsky et al. ...... 382/115 |
| 6,792,418 | B1 | * | 9/2004 | Binnig et al. ............. 707/3 |
| 7,076,430 | B1 | * | 7/2006 | Cosatto et al. .......... 704/275 |

OTHER PUBLICATIONS

U.S. Appl. No. 09/239,845, "A Virtual Map System and Method for Tracking Objects".
U.S. Appl. No. 09/079,754, "Apparatus and Methods for User Recognition Employing Behavorial Passwords".

* cited by examiner

Primary Examiner—Michael N. Opsasnick
(74) Attorney, Agent, or Firm—Rafael Perez, Esq.

(57) ABSTRACT

A system and method of interpreting communicative behaviors including actions, gestures and sounds produced by individuals, the system includes a database of stored behavior codes, each behavior code having an associated explanation; the system can access the database, records a behavior performed by the individual, assigns an observed behavior code to the recorded behavior, compares the observed behavior code to the stored behavior codes in the database of stored behavior codes, and retrieves the explanation associated with the stored behavior codes which match the observed behavior code. The system can also recognize events and correlate recognized events to the individual's behavior's.

29 Claims, 7 Drawing Sheets

TRANSLATOR FOR INFANTS AND TODDLERS

FIELD OF THE INVENTION

This invention relates to a system and method of interpreting gestures and sounds produced by individuals in general, and, in particular, to a system and method for recording, and processing gestures and sounds produced by individuals, comparing the processed recordings to a database of interpreted gestures and sounds, and providing caretakers of the individuals with interpretations of the gestures and sounds.

BACKGROUND OF THE INVENTION

The interpretation of nonverbal communication, i.e. gestures and sounds, is crucial for the care taking and treatment of nonverbal individuals. Young children who have not yet learned to speak use behaviors such as movements, gestures and sounds to express their needs and current state of emotions and well being. Nonverbal communication is often the only means of expression for individuals with hearing loss, autism and other disorders and illnesses. Even for verbal individuals, nonverbal communication, if interpreted properly, can be used to recognize, diagnose and track treatment of medical disorders.

From time immemorial, parents, as an example, have been faced with the challenge of determining the meaning behind gestures and sounds produced by their nonverbal infants and toddlers. New, inexperienced parents resort to trial and error to determine what need the child is expressing. Experienced parents and care givers often encounter nonverbal communicative behaviors with which they are not familiar. Child and parent are apt to experience frustration upon erroneous interpretations of the child's nonverbal communications. The child's frustration masks the actual need being expressed. The parent's frustration is sensed by the child and will interfere with making a proper interpretation of the child's communications. The frustrations can bring on undesirable behaviors on the part of the parent or child. Within time, the inexperienced parent will usually learn to intuitively recognize patterns and correctly interpret their child's nonverbal communications with which they are familiar. In most cases the frustration could have been avoided by providing the inexperienced parent with the knowledge accumulated by experienced caretakers. However, there is no effective means for a parent to discover caretakers who have experience with the particular behavior the parent is having trouble interpreting. Therefore, there is a need for a system and method to provide caretakers of individuals with access to knowledge of nonverbal behavior accumulated by experienced caretakers for interpreting nonverbal communicative behavior of nonverbal individuals.

However, there are instances in which a nonverbal communication is not contained within the knowledge already accumulated. The gesture, sound or movement recognized may be particular to the individual child or may indicate a condition which does not fall within the norm. It is probable that the interpretation of the nonverbal communication, once discovered, will be of aide to a caretaker at some point in the future. Therefore, there is a need for a system and method for tracking previously unrecognized behaviors of individuals until an interpretation is discovered, and adding the newly interpreted behavior to the already accumulated knowledge.

There are instances in which an individual's nonverbal communication is related to current situational conditions such as an event or an object proximate to the individual. It is difficult for a caretaker of the individual to account for the variable events or objects which might be affecting the individual under their care, making it difficult for the caretaker to associate the individual's behavior with an event or object. Therefore, there is a need for a system and method of associating events and proximate objects to the behaviors of an individual.

Once a behavior occurs, it is difficult for care givers and caretakers to compare it with other behavioral occurrences and to associate it with situational conditions. Each behavior is a composite of many factors. Tracking each factor of a behavior is confusing and time consuming. A caretaker may not be capable of tracking proximate events or objects for the purposes of association with the behavioral occurrences, particularly when the association is not obvious. In addition, the process of observing for the purpose of recognizing repetitive behaviors takes care givers and caretakers away from their other duties and responsibilities. Furthermore, it is difficult for a parent to be objective about their own child's behavior and to see it realistically. Therefore, there is the need for a system and method for recognizing a repetitive behavior and studying it through observing it repetitively and analyzing it.

It may be impossible for a parent or care giver to observe or study a child's behavior from the same place where the child is located. Therefore, there is a need for a system and method to provide the ability to observe the behavior of an individual from a location remote from the individual.

There are situations in which a caretaker cannot guard the individual under their care from every danger in the environment. For example, the caretaker may be caring for more than one individual, may be distracted while performing one of their duties, may be unfamiliar with dangers in the environment, may be caring for an individual who tends to sneak and seek out trouble, etc. Therefore, there is a need for a system and method of alerting a caretaker when an individual under their care is exposed to potential danger.

In summary, there is a need for a system and method for providing a caretaker of an individual with the ability to identify nonverbal behaviors of an individual under their care by comparing and matching the behavior with a collection of previously recorded nonverbal communicative behaviors, for associating nonverbal behaviors to situational conditions, for recognizing patterns of behavior and associating situational conditions to the behavioral patterns, and for alerting a caretaker when a nonverbal behavior poses a danger.

SUMMARY

It is an aspect of this invention is to provide a system and a method for recognizing nonverbal behaviors performed by an individual, comparing the recognized behavior to a collection of known behaviors and learning from the known behaviors what may be causing the recognized behavior and what can be done for the individual.

Another aspect of this invention is to provide a system and a method for determining when a relationship exists between events and behaviors.

Another aspect of this invention is to provide a system and a method for detecting the occurrence of a dangerous event, and detecting behaviors indicating that an individual is in serious trouble due to the occurrence of a dangerous event and alerting a caretaker of the individual appropriately.

Another aspect of this invention is to provide a system and a method for providing caretakers of individuals with access to information collected relative to known behaviors and their causes, and for providing the means for caretakers to communicate with one another and with experts in appropriate fields.

To accomplish the above and other aspects, a method is proposed, which, in the preferred embodiment, comprises the steps of observing and recording a behavior of an individual; assigning a code to the observed behavior; comparing the observed behavior code with a database of behavior codes associated with known behaviors; retrieving an explanation associated with the known behavior codes which match the observed behavior code; correlating related events to the observed behavior; providing access to information stored about various behaviors, events and their relationships and providing means for caretakers of individuals to communicate with one another and with appropriate experts. The method may further include the steps of sending an alarm upon the occurrence of an event which poses a danger to the individual; and sending an alarm upon recognition of behaviors of the individual which indicate that the individual is in danger.

In addition, a system is proposed, which, in the preferred embodiment, comprises a recording means for recording a behavior performed by an individual, the recording means being in communication with a user interface; and an Analysis Provider in communication with the user interface, the Analysis Provider having a database of behavior codes associated with known behaviors, and associated with each behavior code is an explanation and event data regarding events related with each known behavior. The Analysis Provider may further have a) a Behavior Code Module for recognizing a recorded behavior and associating a behavior code with the recognized behavior, and b) a Behavior Code Matching Module for finding behavior codes associated with known behaviors which match the recognized behavior code, and retrieving information associated with the known behavior code from the database. Furthermore, the Analysis Provider may include a Situational Analyzer for identifying and tracking the occurrence of events which can be correlated to the recognized behavior, for recognizing repeated behavior patterns of the individual behaviors, and for recognizing when an event occurs which poses a danger to the individual.

DETAILED DESCRIPTION OF THE INVENTION

In the following description, the terms "server" and "database" are used in a generic functional sense. The term "server" should be understood within the client/server architectural model—the client requests a service, the server provides a service. The term "database" can be understood in its most broad definition as a data structure stored on one or more pieces of hardware. A "database" and "server" may be depicted as one entity labeled a "database" which is inclusive of the "server", yet it is to be understood that the "database" functions to store data and the "server" functions to provide access to the "database". Indeed, any of the servers or databases could be implemented using a distributed network system, where the functional elements of a server or database are not only distributed among nodes, but will often migrate from node to node. On the opposite end of the spectrum, all of the servers and databases discussed below could be resident on one computer. However much of each server or database is implemented in software, firmware, or hardware being also open to many variations, as is well known in the art.

Furthermore, the terms "network" and "computer" are used in the most general sense. A "computer" is any computing means, from a single microprocessor or micro controller to a computer system distributed over multiple processing nodes. A "network" includes any means that connects computers. Thus, although the preferred embodiment uses the Internet, the nodes could connect through any other type of Intranet or network such as a central server with individual point-to-point connections, a LAN, etc.

The term "caretaker" refers to one who takes care of or gives care to another individual such as a parent, a baby sitter, a teacher, a care giver, a doctor, a therapist, a nurse, etc. The term "care giver" refers in particular to those involved in the temporary care of an individual for providing a specialized service on a patient/client basis.

The terms "nonverbal behavior", "nonverbal communication", and "nonverbal communicative behavior" refer to movements, gestures and sounds (including gestures accompanied by words) produced by an individual intentionally or unintentionally and which express a need, desire, or current state of emotional, mental or physical well being of the individual.

Other terms in the text are also to be understood in a generic functional sense, as would be known by one skilled in the art.

Figure 1:
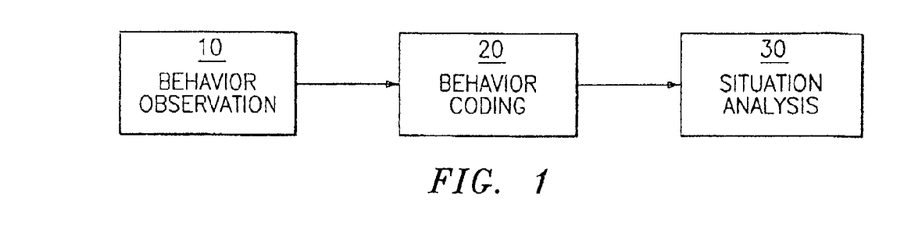
FIG. 1 is a block diagram of the fundamental modules of a preferred embodiment of the present invention.

The procedure according to the preferred embodiment of the present invention is depicted in FIG. 1. In the first stage, Behavior Observation 10, a nonverbal behavior or series of nonverbal behaviors is observed. The second stage, Behavior Coding 20, involves associating a code with each behavior observed. The Behavior Code associated with each behavior observed is then compared to a collection of stored Behavior Codes. Each Behavior Code in the collection of stored Behavior Codes has an associated explanation regarding the cause of the behavior. When a suitable match is found, the explanation associated with the stored Behavior Code is retrieved and presented to the caretaker. If a suitable match is not found the Behavior Code associated with the observed behavior can be added to the collection of stored Behavior Codes. In the third stage, Situational Analysis 30, events and objects are recognized and correlated to the observed behavior.

Data gathered at the first stage is passed to the next stages. Although the second and third stages will be described in the preferred embodiment as being managed by one entity providing a service over the Internet, each stage could be handled by a separate entity. In other words, in the preferred embodiment, a single service provider is managing the second and third stages for subscribers. However, these functions could be delegated to a service provider or company who provides the service of one or more of behavior observation, behavior coding or situational analysis. Furthermore, each or all of these services could be offered to a client by a single company or a combination of companies utilizing conventional methods other than the Internet for delivering information between the client and the company.

Figure 2:
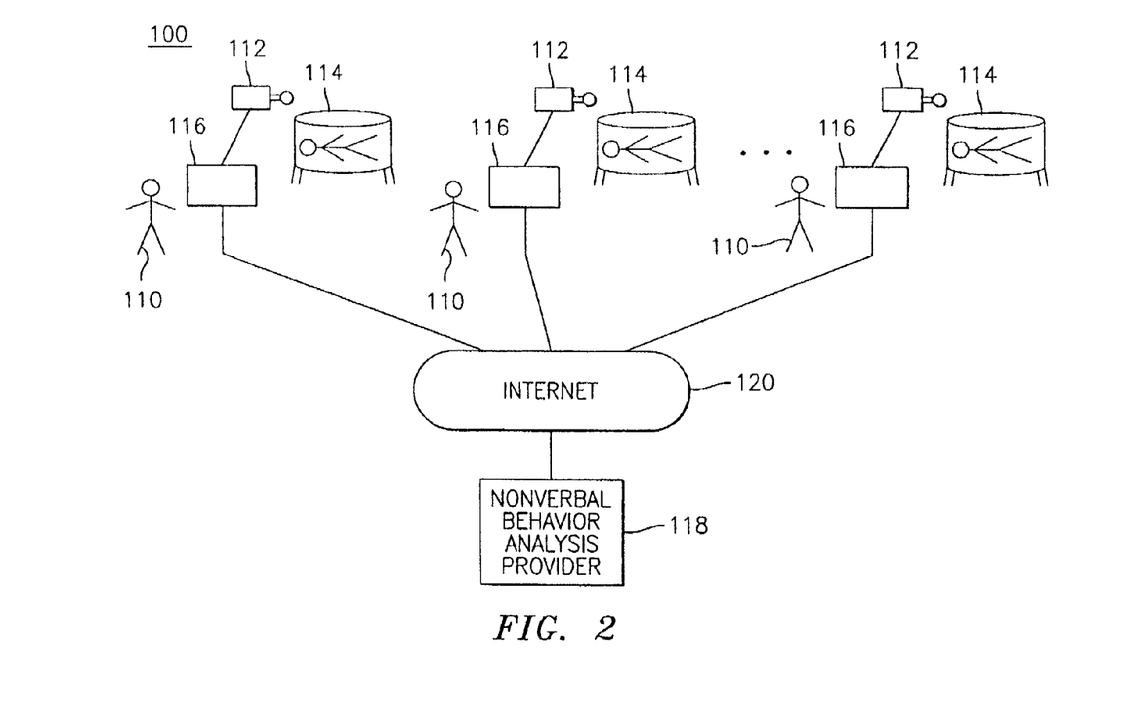
FIG. 2 is a diagram of a system according to the preferred embodiment of the present invention.

FIG. 2 is a diagram depicting the preferred embodiment of the system for providing the services shown in FIG. 1. As shown, a caretaker, who is a user 110 to the service provided by the system, operates recording means 112 for creating representations of nonverbal behaviors performed by an individual 114. A user interface 116 is provided for allowing the user to communicate through, for example, Internet 120 with a Nonverbal Behavior Analysis Provider Server (AP) 118. The user operates the user interface 116 to submit selected portions of the representations to the Analysis Provider 118 for analysis.

The recording means 112 can comprise a device or manual means for recording a representation of an individual's behavior. The representation can be in any format such as textual, pictorial, graphic, digital or oral description or combination thereof. Devices employed as recording means can be an analogue or digital camera, video camera, thermal imaging system, ultra sound imaging system or any system which records a representation of the behavior of the individual. The device can be switched on and off manually or by automatic means such as the user interface 116 or a motion detector. The device can store recordings in files or submit them to the user interface 116 as they are being recorded.

The user interface 116 is any means for providing communication between the user and the Analysis Provider 118. The communication can be in any format such as written, verbal or electronic. The communication can be man to man, man to machine or machine to machine. The user interface 116 can further comprise carrier mail, a telephone, a wireless telephone, or a computer such as a personal or hand held computer. In the preferred embodiment, the user interface 116 and/or the recording means 112 comprise computers and store the recordings in files. The files can be reviewed and segments from the files can be selected for transmission to the Analysis Provider 118. Furthermore, in the preferred embodiment, the user interface and/or the recording means are capable of selectively allowing recordings to be transmitted to the Analysis Provider 118 as they are being recorded. In the preferred embodiment the user interface 116 communicates with the Analysis Provider 118 via the Internet 120. However, communication can be provided by an Intranet connection or any known type of network. Alternatively, information being transferred between computers comprising the user interface 116 and the AP 118 is stored on a conventional storage device and transported between the user interface 116 and the Analysis Provider 118.

In the preferred embodiment, the user interface 116 and the recording means are in communication. This communication can be provided by cable connections or by wireless connections.

Alternatively, the behavior can be observed directly by the Analysis Provider. This eliminates the need to form a representation of the behavior and provide it to the Analysis Provider.

The Analysis Provider can be a system comprised of personnel and/or devices for receiving recordings, recognizing behaviors and events, associating codes to the behaviors and events, and analyzing the events and behaviors. In the preferred embodiment the Analysis Provider 118 is a computer having or having access to a database of behavior codes.

The Analysis Provider 118 provides a service to a user 110. The user 110 can be a single individual or a plurality of individuals. The user 110 is generally a care giver or an assistant to a care giver of the individual whose behavior is being analyzed. The service provided by the Analysis Provider 118 can be provided gratis or for a fee. The fee can be variable according to user requests, such as the extent of analysis and reporting requested by the user 110. The Analysis Provider 118 can require that a user register with the service prior to using the service.

In the preferred embodiment the service provided by the Analysis Provider 118 includes receiving a representation of a behavior from a user, associating a code with the received behavior representation, comparing the received behavior code with a collection of stored behavior codes, returning an explanation associated with the stored behavior codes which match the received behavior code to the user.

Figure 3:
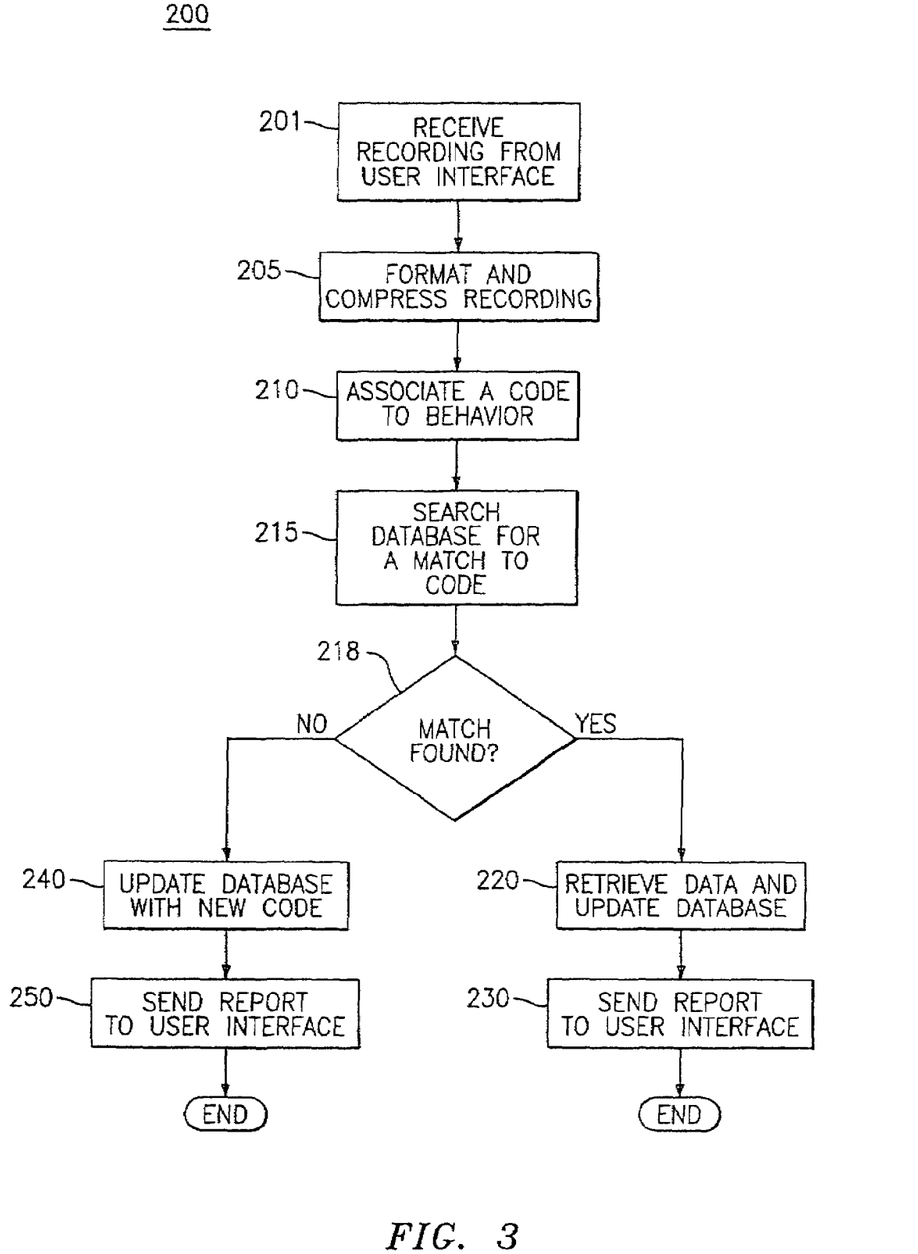
FIG. 3 is a flowchart of a method according to the preferred embodiment of the present invention.

A general outline of the basic steps performed by the Analysis Provider 118 in the preferred embodiment of the inventive system is shown in FIG. 3. In step 201, the Analysis Provider receives a representation of the behavior to be analyzed from the user interface 116. The representation is an image and sound recording comprising a string of frames. Alternatively, the representation can be only an image recording. The representation may be in analog or digital form. In step 205 the recorded representation is formatted into a digital format comprising a string of digital frames and then compressed into a file. The file is compressed for preserving space, and for providing a schematic representation of the image which can be broken down for analysis. In the preferred embodiment the file is compressed by sampling the string of formatted digital frames at regular intervals and storing the sampled frames with a time stamp. Each sampled frame is then stored as a multidimensional vector. Any known method can be employed for digitizing and compressing the images. Sampling can be done at irregular intervals. Inactivity can be filtered out.

In step 210 a behavior code is associated with each behavior represented in the compressed file. The Analysis Provider 118 recognizes gestures and uttered sounds which make up a behavior. Upon recognition, a code for each recognized gesture and sound is provided. When a gesture or sound is not recognized, a new code can be provided. The codes for the gestures and sounds are used to form the behavior code. In another embodiment, only gestures are recognized and assigned codes for forming the behavior code.

An example of a recognition system for identifying individuals according to their gestures and text independent speech is U.S. patent application Ser. No. 09/079,754 having the same assignee as the present application, entitled "APPARATUS AND METHODS FOR USER RECOGNITION EMPLOYING BEHAVIORAL PASSWORDS", the disclosure of which is incorporated herein by reference. In one embodiment of such a recognition system, behaviors comprised of a series of gestures are recognized. Each gesture is recognized by clustering similar frames of a compressed digital file of images into a cluster, and grouping the clusters into strokes. A stroke is a series of frames which represent an individual performing a particular gesture. The strokes are classified and labeled into gesture symbols which are then interpreted to form a gesture unit.

The Analysis Provider 118 assigns a code to each gesture unit. The codes assigned to the series of gesture units which make up the behavior are assigned to the behavior code for that behavior. Similarly, the sounds of the behavior are broken up into sound units which are associated with a code and assigned to the behavior code. Thus, the behavior code is comprised of at least one of a gesture component and a sound component, each component being comprised of at least one unit code.

The gesture units are further broken up into property units such as which body part was moved, what type of movement was performed, the individual's body position and the duration of the gesture unit. Each property unit is assigned a code. The property codes assigned to the property units comprising a gesture unit are concatenated to form the gesture unit code. The sound unit will likewise be broken up into property units such as sound pitch, sound volume, sound quality, and the duration of the sound unit, and may include units appropriate for automating speech recognition (as known in the art). The property unit codes assigned to the property units comprising a sound unit are concatenated to form the sound unit code.

The behavior can be broken down into gesture units and sound units in various ways, as for example according to predetermined time intervals or according to the recognition of the end of a gesture or sound. The codes assigned to the gesture and sound units are integrated into one behavior code comprising a string of integrated gesture unit and sound unit codes. Alternatively the gesture component and the sound component of the behavior code can be maintained as separate components associated with one behavior, each component comprised of a string of corresponding unit codes.

The behavior code can have a hierarchal structure such that specific gesture or sound unit codes are assigned priority levels. There are a variety of criteria according to which priority levels are assigned to behavior unit codes. Examples of criteria include chronological order, frequency of occurrence within the behavior code database, degree of dominance, etc. . . . The degree of dominance refers to the degree to which a behavior unit is associated with the causes of the behavior. An expert, such as a behavioral psychologist, would determine the degree of dominance of a behavior unit. For example, an expert might attribute a higher degree to a behavioral unit representing head banging than to a behavioral unit representing toe wiggling.

Similarly, the property unit codes are assigned selectable priority levels. The priority levels are assigned according to the degree to which a property unit distinguishes one behavior from another for the purposes of finding a match when searching the behavior codes database.

The priority levels assigned to behavior unit codes and property unit codes is selectable and can be determined by operators of the system and experts in the behavioral or medical fields. The selections can be made manually or automatically. The selections can be dynamic, such that the selections change as other factors change, such as new data being added to the behavior code database. The priority is selected in accordance with data stored in the individual and/or general behavior codes databases.

In step 215 a behavior code database containing a collection of stored behavior codes is searched for behavior codes which match the assigned behavior code. The database is comprised of multiple records. Each record corresponds to one behavior code. Each record has multiple fields containing data pertinent to the record.

In the preferred embodiment the search will account for priority levels within the structure of the behavior codes. Behavior unit codes having a higher priority will be searched for prior to those of lower priority. Likewise, property unit codes having a higher priority will be searched for prior to those of lower priority.

In the preferred embodiment the criteria are specified for the degree of similarity desired for determining a match between the assigned behavior code and behavior codes within the database. The criteria for match determination can be specified by operators of the system or by the user.

Upon determination of at least one match at step 218, step 220 is then executed. At step 220 data is retrieved from each record having a matching behavior code. Included in the data retrieved from the matching records is an explanation of the behavior represented by the matching behavior code. The explanation preferably is a textual segment entered previously by a user of the system or by an expert consultant. At step 230 a "match found" message comprising data retrieved from the matching records is transmitted to the user.

In the instance where a match is not found, step 240 is executed. At step 240, with the user's consent, the assigned behavior code is added to the database of behavior codes together with appropriate data to form a new record. The explanation field of the data record can be left blank at this time and filled in at a later date if desired.

In the preferred embodiment, users of the service provided by the inventive system first subscribe to the service by registering with the Analysis Provider 118. The user 110 provides the Analysis Provider 118 with personal information which is entered into a subscriber database. An identification (subscriber ID) code is assigned and stored by the system for each user registered as a subscriber. Subscriber data relating to financial information is kept confidential. The subscriber can have the option to allow or prevent access by other subscribers to information such as name, e-mail address, phone number and occupation. In other embodiments the service provided by the inventive system could be available to the public. Public users and subscribers would then have various levels of access to the information provided by the service.

The behavior code database can refer to a general behavior code database for storing behavior codes associated with behaviors performed by a variety of individuals, and/or to an individual general behavior code database for storing behavior codes associated with behaviors performed by the individual. The individual database is preferably stored by the AP 118, or by the user interface 116. The means to search and update the database is also preferably resident at either the AP 118 or the user interface 116.

Figure 4:
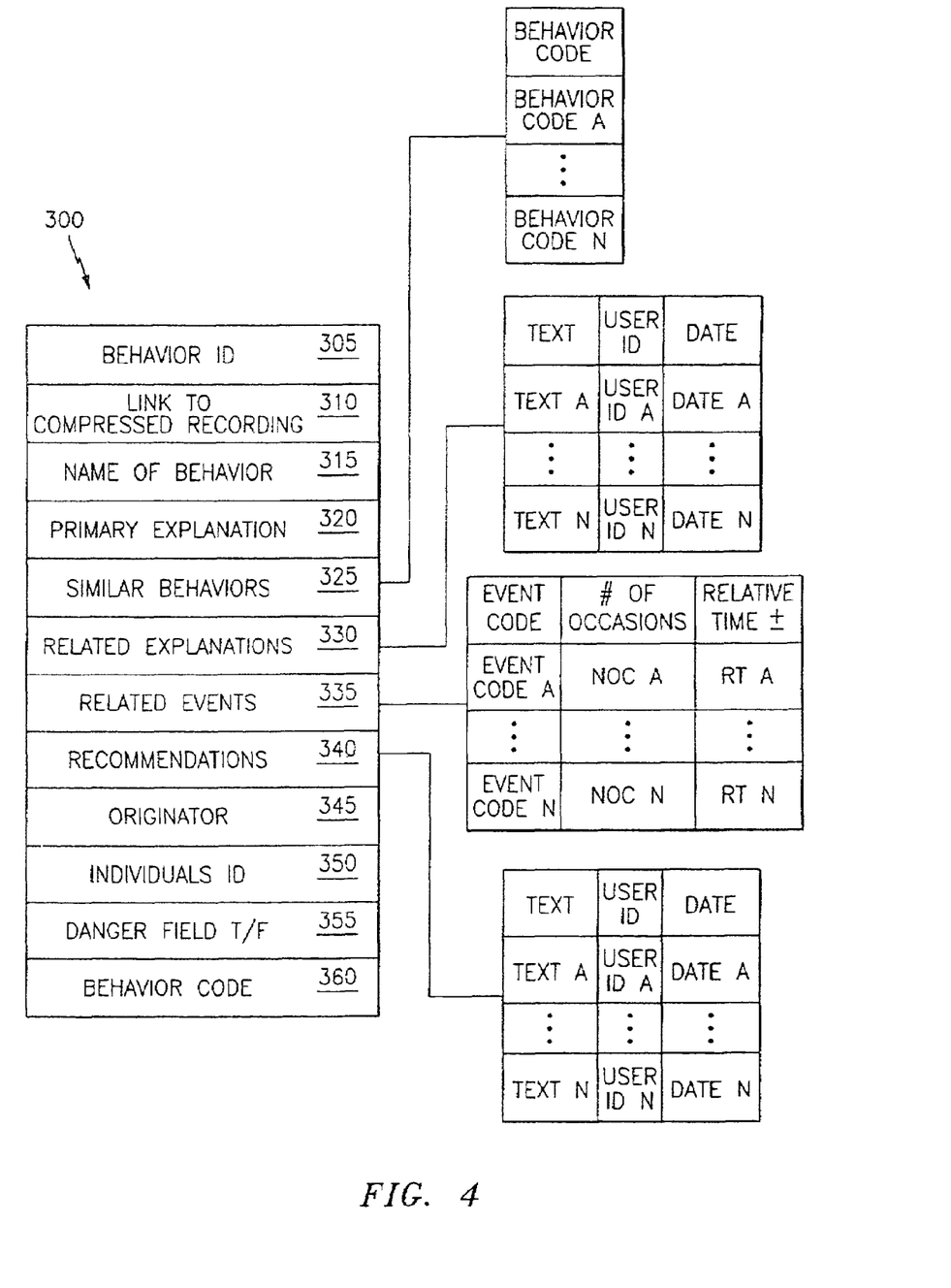
FIG. 4 is a diagram of exemplary fields in a Behavior Code Database record according to the preferred embodiment of the present invention.

The behavior code database is structured in a variety of ways. FIG. 4 shows the structure of an exemplary data record of the general behavior code database. The behavior code record contains, for example, fields for an identification number (behavior ID) for the behavior represented by the behavior code; links to other databases storing the files of the recordings of the behavior; a name for the behavior; the behavior code; an identification number for the subscriber who originally entered the behavior into the database (originator ID); a date of original entry; a primary explanation for the behavior; a link to a list of other explanations; a link to a list of event data related to the behavior, event data including, for example, the number of occurrences of each event associated with the behavior recorded, the date and time of each event occurrence, a list of subscriber IDs who submitted a behavior related to the event; a link to a list of recommendations to the caretaker of the individual displaying the behavior; a link to a list of similar behavior codes and their ID's. These fields are only examples, and the behavior code records may contain many more or a subset thereof.

Preferably, the recordings of the behavior are stored and indexed according to the behavior ID. By storing the recordings, they can be referred to for viewing or further analysis, and can be deleted when no longer needed. The recordings are stored in any format such as the format in which they were received or as a compressed file.

In the preferred embodiment, the lists are linked databases having keys stored in fields of the records of the behavior code database. Each list contains multiple records. For example, records in the list for explanations, list for possible causes or list for recommendations may contain multiple records each having fields for a textual entry, a subscriber ID for the subscriber who entered it, and a date of entry. The list of similar behaviors may contain multiple records each having a field for a behavior ID. A user viewing a record containing a behavior ID or subscriber ID uses the ID to look up the behavior or subscriber in their respective databases in order to retrieve more information.

Access to the Analysis Provider 118 is provided by the user interface 116. In the preferred version a user 110 uses a web browser program, such as Netscape Navigator™, to provide access to the Internet 120 for accessing the Analysis Provider 118. The user 110 exchanges information with the AP 118 via Web pages. The information being transmitted to and from the Analysis Provider 118 is protected for confidentiality by employing encryption and decryption techniques such as SSL (Secure Sockets Layer) if desired.

Prior to a user 110 submitting recordings of behaviors performed by an individual, the user 110 must provide the Analysis Provider 118 with information about the individual 114. The information is stored by the Analysis Provider 118 or by the user interface in an individual personal data file or database. The information may need to be updated periodically. The Analysis Provider 118 prompts or requires the user 110 to update the information at specific time intervals, in particular for individuals 114 whose condition is in flux, such as a growing child or an individual with an unstable medical history. Information which must be entered in the individual personal data file for registering an individual 114 may include name, identification number assigned by the system, weight, height and dimensions of specific body parts. The measurements may be entered manually or entered automatically by a measuring device. The AP 118 uses the physical measurements of the individual 114 to scale the compressed file of the image for accurate association of a behavior code. Other information to be entered may be related to allergies, disabilities, present medical condition, a picture, medical history, typical demeanor (appetite, mood, energy level), current demeanor, etc. . . .

After the user enters or confirms updated information about the individual, the user specifies criteria for the analysis of the images to be submitted. The AP then presents the user with questions to be answered, which may depend on answers provided previously. The user is prompted to supply answers in various formats such as by filling in a blank field or by selecting from multiple choices. In the preferred embodiment, the user is presented with a User Analysis Request Web page, such as the page 500 shown in FIG. 5. Information fields that may be too large to show on the Web page are shown on separate pages or pop-up windows by pressing the appropriate button. Lists are shown as scrolling lists or as pop-up windows.

Figure 5:
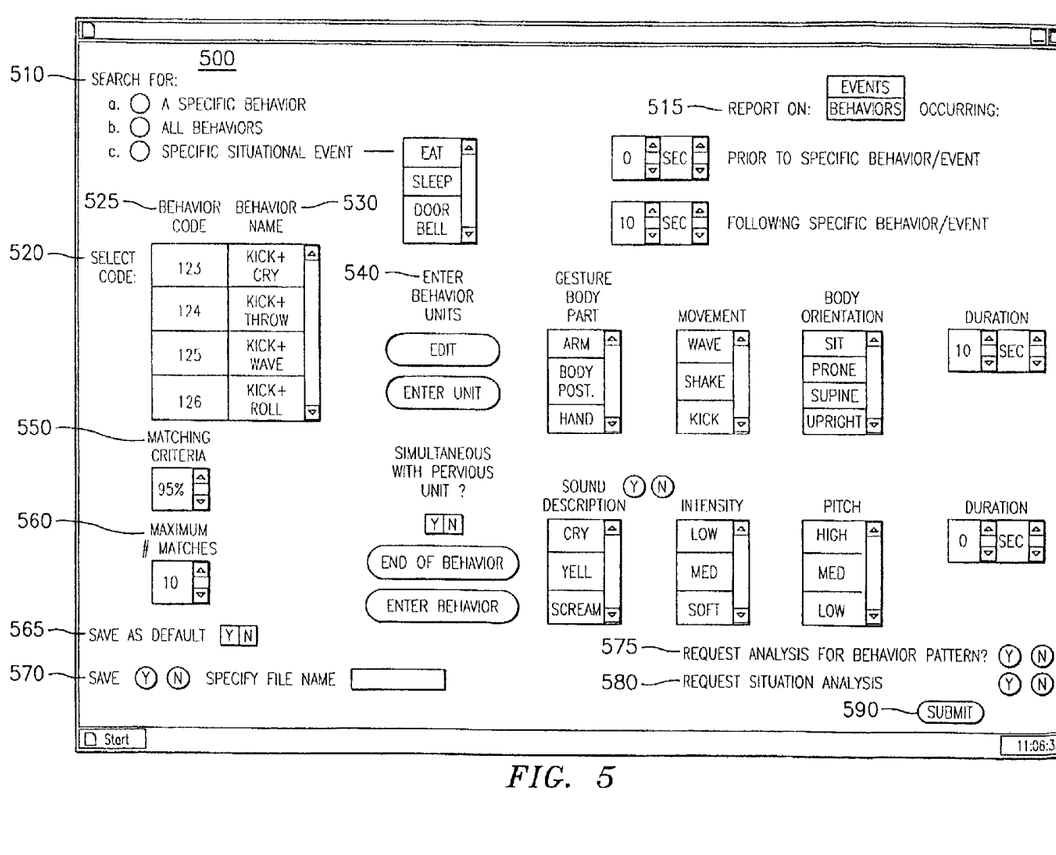
FIG. 5 is an exemplary User Analysis Request Web page according to the preferred embodiment of the present invention.

At section 510 the user directs the analysis to extract from the images submitted: a) a specific behavior, b) all behaviors or c) behaviors related to situational events. At section 515 the user chooses to further extract situational events or behaviors within a selected chunk of time before and after each occurrence of a specified behavior. At section 520 the user describes the behavior being extracted. At field 525 the user enters the behavior code for the specific behavior or behaviors of the behavior pattern being extracted. The code is typically entered by keying the code in to field 525 or by selecting the code from a list of codes and descriptions 535. The description for any code entered is displayed in field 530 in order for the user to confirm that it is the code intended. At field 540 the user selects a series of gesture and sound units separately which comprise a behavior. The gesture unit is broken down, by example, into body part, movement, body orientation and duration of gesture. The user selects "Yes" or "No" of inclusion of a sound unit. The sound unit, by example, is broken into sound description, intensity, pitch and duration of sound. The user then indicates if a gesture or sound unit is simultaneous with the previous gesture or sound unit entered. The code and description which best matches the combination of gesture units selected will pop up in fields 525 and 530 respectively. The user then enters a series of behavior codes which would constitute a behavior pattern. The user selects "End of Behavior" to indicate when a series of behavior units has been entered which constitute the behavior. The user then selects "Enter Behavior" to enter the entire series of behavior units.

The user specifies criteria for the degree of accuracy required in matching the behavior being extracted to behaviors stored in the database. In this example, at field 550, the user selects a percentage of accuracy, however any method could be implemented. A minimum limit to the degree of accuracy can be required. At field 560 the user specifies the maximum number of returned matches desired. The user can store his current selections as a default for future submissions at field 565, and saves the current selections as a file at 570. The user then requests that the behaviors extracted be analyzed for determining if a pattern exists at 575. The user next requests situational analysis of the behaviors and events extracted at field 580 for determining if there is a relationship between the behaviors and events proximate to the behavior or objects proximate to the individual. Finally, once the user has entered the necessary information, the user submits the criteria for analysis entered at 590.

Once the criteria for analysis has been submitted, the file containing the images selected to be analyzed must be submitted, although the order could be reversed.

Figure 6:
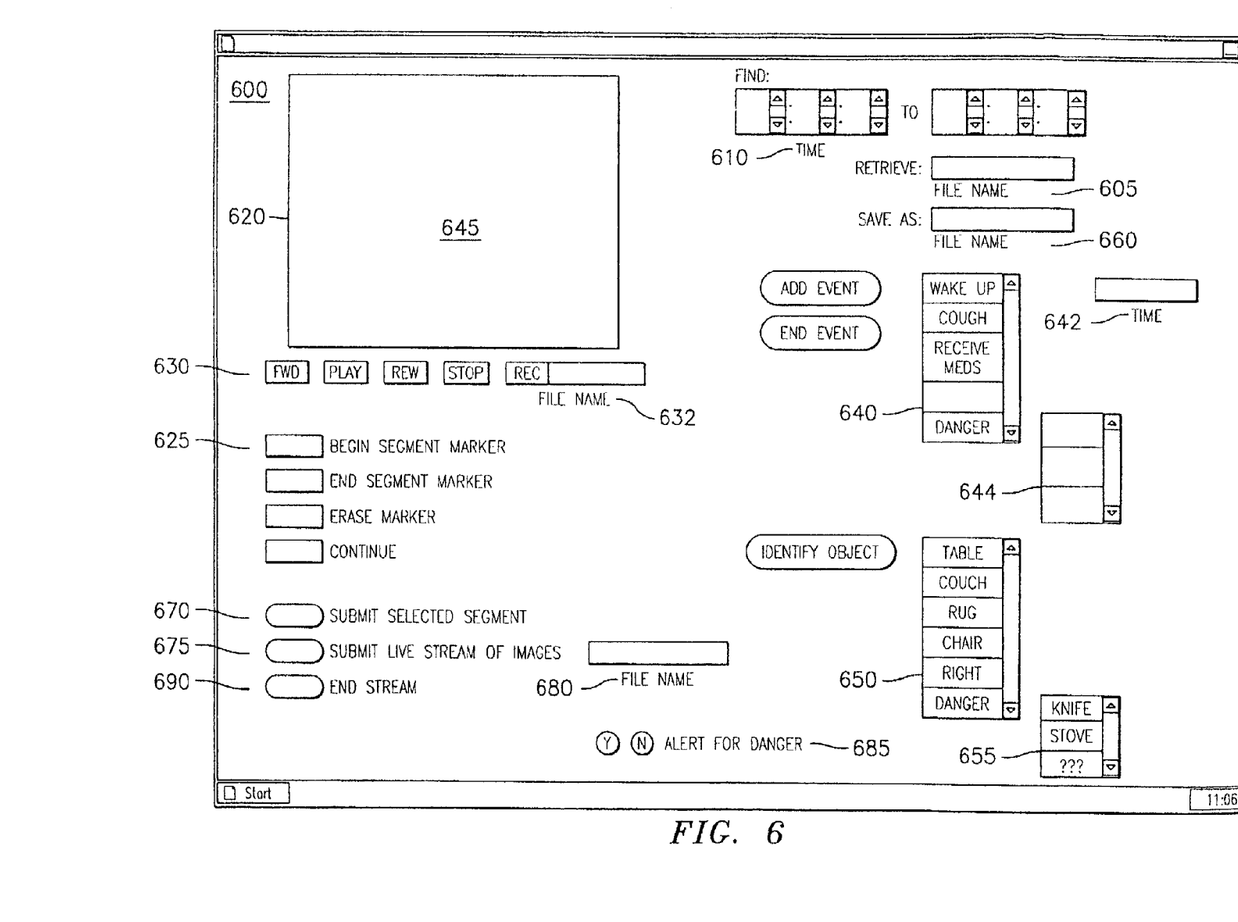
FIG. 6 is an exemplary Submit Recording Web page according to the preferred embodiment of the present invention.

FIG. 6 shows an exemplary screen 600 for a user to select the images to be submitted to the AP for analysis. The user retrieves a file of images stored by the recording means 112 or the user interface 116. The file to be retrieved is specified at field 605. The user specifies a time segment of the file to be retrieved at field 610. A view window 620 is provided for viewing the images. As the user views the images in field 620 he marks the beginning and end of a segment by selecting begin and end segment marker buttons in section 625. In order to select multiple segments, the continue button is used to allow the user to select successive segments. The erase marker button will allow a user to erase a begin segment or end segment marker, together with any marker paired with it. The user controls the display in the view window 620 using the controls in area 630. The user hits the "REC" (record) button to instruct the recording means to record and store its recordings in the file specified at field 632.

The user enters events by selecting an event displayed in the view window 620, selecting "add event" and selecting the appropriate event label from window 640. The time of occurrence will appear in the time window 642. The user specifies the end of the event by selecting "end event". Selecting a "danger" event will allow the user to enter an event which poses a danger from window 644. The user is able to identify objects in the recording by using cursor 645 to point at or select the object displayed in window 620, and selecting the appropriate object label from window 650. Selecting a "danger" object allows the user to enter an object which poses a danger from window 655.

The user saves the selections made by selecting "save" and specifying a file name at field 660. When the necessary information has been entered, the user submits the selected segments to the AP for analysis by selecting "submit selected segments" field 670. Alternatively, the user can choose to submit a live stream of images, as they are being produced by selecting "submit live stream of images" field 675. The filename from which the images are retrieved must be specified in field 680. When submitting a live stream of data, the user has the option of selecting the option to "alert for danger" in field 685. This will cause a screen to be presented to the user in which the user must specify the nature of any dangers which might exist or occur in the vicinity of the individual. The user ends the stream of images by selecting "end stream" in field 690 with the filename specified in field 680.

Figure 7:
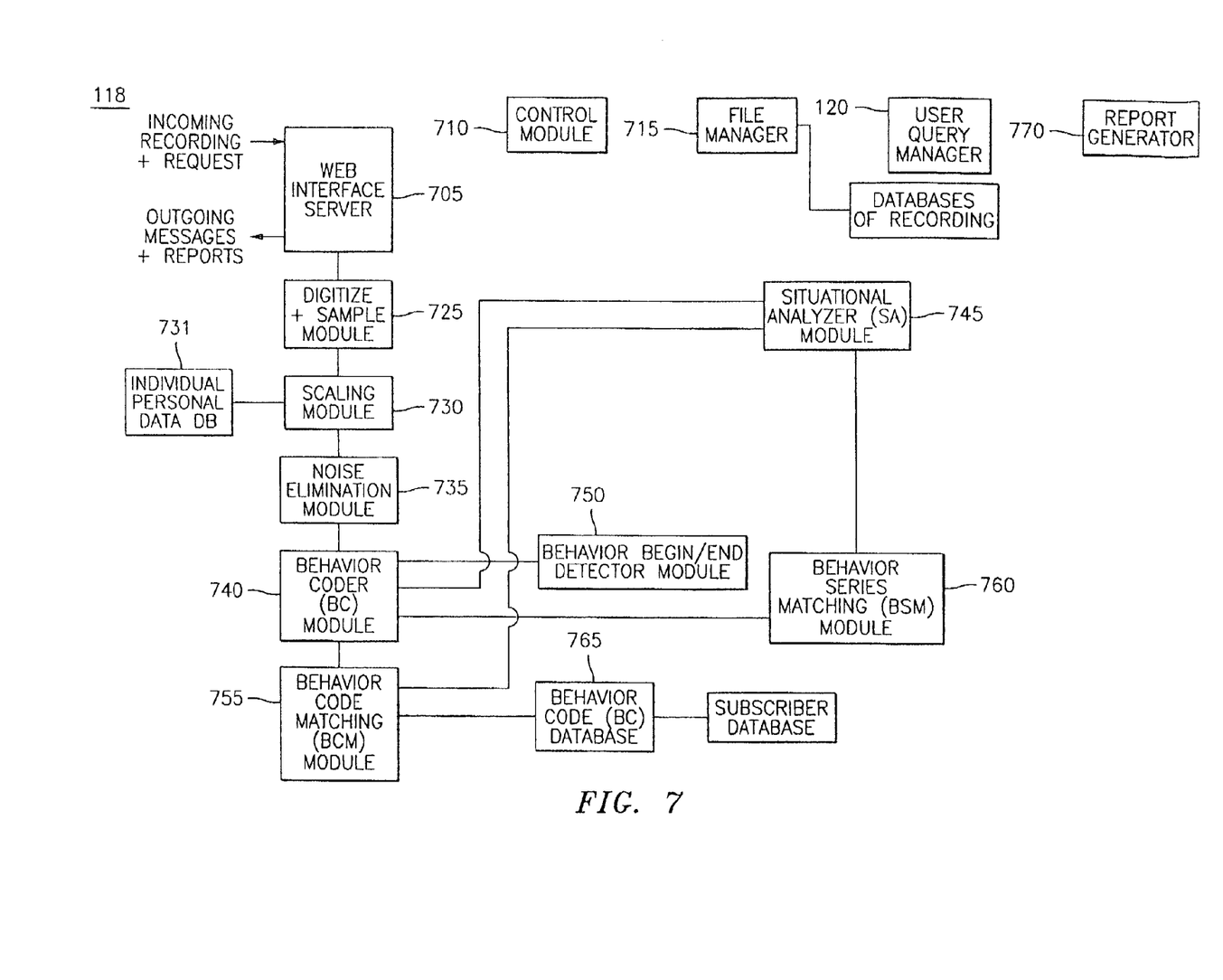
FIG. 7 is a block diagram of the Analysis Provider according to the preferred embodiment of the present invention.

Now, the modules used by the AP 118 to analyze behaviors represented in recordings submitted by the user 110, via the user interface 116, will be described in detail with reference to FIG. 7. The process begins when the request data and the recording data is sent to the AP 118 over the Internet 120. As mentioned above, information transmitted via the Internet can be secured via encryption/decryption techniques which are commercially available. The incoming data, including request data entered by the user and recording data is received and handled by the Web Interface Server 705. All data being sent to and from the AP 118 is handled by the Web Interface Server 705.

The Control Module 710 supervises the passage of control from one module to the next. The File Manager 715 is responsible for supplying each module with the proper file or segment of a file to be processed. The File Manager accesses databases of submitted recordings and compressed, digitized formatted recordings. Recording databases are provided for storing the recordings at the desired stages of processing.

The request data entered by the user 110 via web screens at the user interface 116 is sent to the Control Module 710. The Control Module supervises the flow of control in order to fulfill the user's requests. Control is first sent to the Digitize and Sample Module 725. The recording data file is sent by the file manager to the Digitize and Sample Module 725.

The Digitize and Sample Module 725 converts any analogue data to digital data, and compresses the recording data by sampling the frames of the image data and sound data and saving the sampled frames in a compressed image file. Each sampled frame is time stamped. The Digitize and Sample Module 725 can remove segments of image data in which there is no activity, i.e. the frames are identical. Removal of inactivity segments can be done either prior to, or post sampling.

Next, the compressed image file and control is sent to the Scaling Module 730 in which data from the individuals's personal data file, in the individual personal data database 731, pertaining to the measurements of the individual, is accessed for providing a scaling factor. The Scaling Module can either provide the scaling factor or actually scale the images. The scaled and compressed image file and control is sent to the Noise Elimination Module 735 for eliminating frames or portions of frames in which non-meaningful activity exists. The Noise Elimination Module 735 can consult a library of non-meaningful activities, or determine that an activity detected is non-meaningful. For example, devices in an infant's room or in a hospital room may be in motion or produce noises which are not related to the behavior of the individual. Examples of devices include a respirator, a clock ticking, a rotating mobile in perpetual motion, etc. . . .

The control unit and file manager will pass control and send the scaled compressed recording file to a) the Behavior Coder (BC) Module 740 when behaviors in the recording file are being analyzed, or to b) the Situational Analyzer 745 when events in the recording file are being analyzed.

When the scaled compressed recording file is received by the Behavior Coder Module 740, the compressed recording file is examined for recognizing gestures and sounds which make up a behavior. The gestures can be further grouped into gesture units, and the sounds further grouped into sound units. Each gesture and sound unit is assigned a code. The gesture unit code can comprise multiple parts such as body part moved, type of movement, position of body and duration of movement. The sound unit code can comprise multiple parts such as sound description, sound intensity and duration of sound. A Behavior Begin/End Detector Module 750 is consulted by the Behavior Coder Module 740 for determining the end of one behavior and the beginning of the next. The gesture and sound unit codes are combined to form a recognized behavior code for each behavior recognized. The combining of the gesture and sound units to form a code for a behavior can be done in a variety of ways. For example, a Synchronizer Module (not shown) can be used for synchronizing the gestures and sound units to best model the actual behavior. In a different method, the gesture units may be stored separately from the sound units. Also, the gesture and sound units may be stored consecutively according to chronological order, with an additional gesture or sound unit code part for indicating when a unit code is simultaneous with the previous unit code.

At this point, the Control Module 710 will pass control to the Behavior Code Matching Module 755 when each recognized behavior code provided by the BC Module 740 is to be compared to existing behavior codes for finding a match. On the other hand control will be passed to the Behavior Series Matching Module 760 when a series of behaviors is to be compared to existing series of behaviors for finding a match.

The Behavior Code Matching Module 755 determines if the user requested that a specific behavior be searched for. In this case, the recognized behavior code is compared to the specific requested behavior code to determine if a match exists. The results are sent to the Report Generator 770. Otherwise, the Behavior Code Matching Module 755 searches a Behavior Codes (BC) Database 765 to find a stored behavior code which matches the recognized behavior code.

When searching the Behavior Code Data Base 765 for a match, an algorithm is used for prioritizing the comparison of gesture or sound units, or their parts. Many different algorithms could be used. For example, a first high priority class may be formed of all behavior codes in the Behavior Code Database having a first gesture unit with a body part moved which matches the body part moved of the first gesture unit in the recognized Behavior Code. A subclass can be formed from the first class by matching first gesture units having the same movement. The subclass can be further narrowed down by matching first gesture units with a body position and then narrowed further by matching gesture units with a duration within a specified threshold. The comparison can proceed by comparing gesture units in their chronological order. Subsequent subclasses can be formed until matches have been found. In a different algorithm, certain types of body parts and movements would have priority and are compared first, regardless of their chronological order. Duration of a movement or sound may or may not be compared until late in the search or not at all.

Just as the recognized behavior codes can be determined by using a module to synchronize the gesture and sound units or consider them separately, the process of searching for a match can also involve comparing gesture and sound units in a synchronized fashion or separately form one another.

Determination of a match is made according to criteria which are selectable. The criteria is selected by the operators of the system, by the system software, by the user or by any combination thereof. For example, the user may have specified that the criteria for a match be a perfect match, such that all of the components of all of the behavior units match. In another example, the user may have specified that criteria for a match be less than perfect, such as 80%. The degree to which codes match one another can be calculated in various ways. For example, the match between a recognized behavior code and a stored behavior code can be assigned a value. The match value can be assigned a beginning value of 100%, which is then decreased a specified amount for each part of a behavior unit which doesn't match, or for matching gesture and sound units which occur in a different order. The match value can be decreased an even greater value when an entire behavior unit in a stored code doesn't correspond to a behavior unit in the observed code.

When control is transferred to the Behavior Series Matching Module 760 it is determined if the user is searching for a specified behavior series. If so, the recognized behavior codes as a string of codes are compared to the specified behavior series and the results are sent to the Report Generator 770 or to the SA Module 745 for further analysis.

Preferably, the Behavior Code Database comprises a general behavior code database and an individual behavior code database. The general behavior code database stores codes associated with behaviors of multiple individuals. The individual behavior code database stores codes associated with behaviors of the individual being observed. The individual behavior database is used, by example, for detecting patterns of the same behavior by the individual. The individual behavior database is stored at the user interface or at the AP, together with computer program code for executing searches and updating data related to the individual database.

The Report Generator 770 receives results from the various modules and generates messages and reports which are sent to the user via the Web Interface Server 705. The user specifies the type of report he wishes to receive, including how detailed it should be, upon registering with the system or submitting a request. The report can be interactive, including the option to proceed with the analysis. For example, the user may be prompted to change the criteria for a match via a user Web screen and then repeat the search. This would be appropriate when no match was found or too many matches were found. The Report Generator 770 may query the user as to whether or not an unmatched behavior submitted by the user can be entered into the BC Database as a new behavior. The Report Generator 770 may further query the user as to whether or not information such as the User's subscriber ID and the individual's ID can be entered into the general behavior code database.

Control is passed to the SA Module 745 for analysis of behaviors and behavior patterns in relationship to events. The SA Module 745 recognizes events and correlates events to behaviors or behavior patterns. An event refers to a) movement of an object, which is distinct from the individual; b) movement of an individual, relative to the object; c) the presence of an object; d) an occurrence in the schedule of the individual; e) an expected occurrence in the schedule of the individual; or f) a detected change in the condition of the individual; in which the above cause a possible influence upon the behavior of the individual. Individual event data such as the individual's schedule and condition are entered into the system either manually by a user, or automatically by a device such as a monitor. Individual event data such as objects present in the images are entered into the system either manually by a user, or automatically by the system via recognition methods. An example of an automatic object recognition system for identifying, monitoring, tracking and/or locating objects is U.S. patent application Ser. No. 09/239,845 having the same assignee as the present invention, entitled "A VIRTUAL MAP SYSTEM AND METHOD FOR TRACKING OBJECTS", the disclosure of which is incorporated herein by reference.

Figure 8:
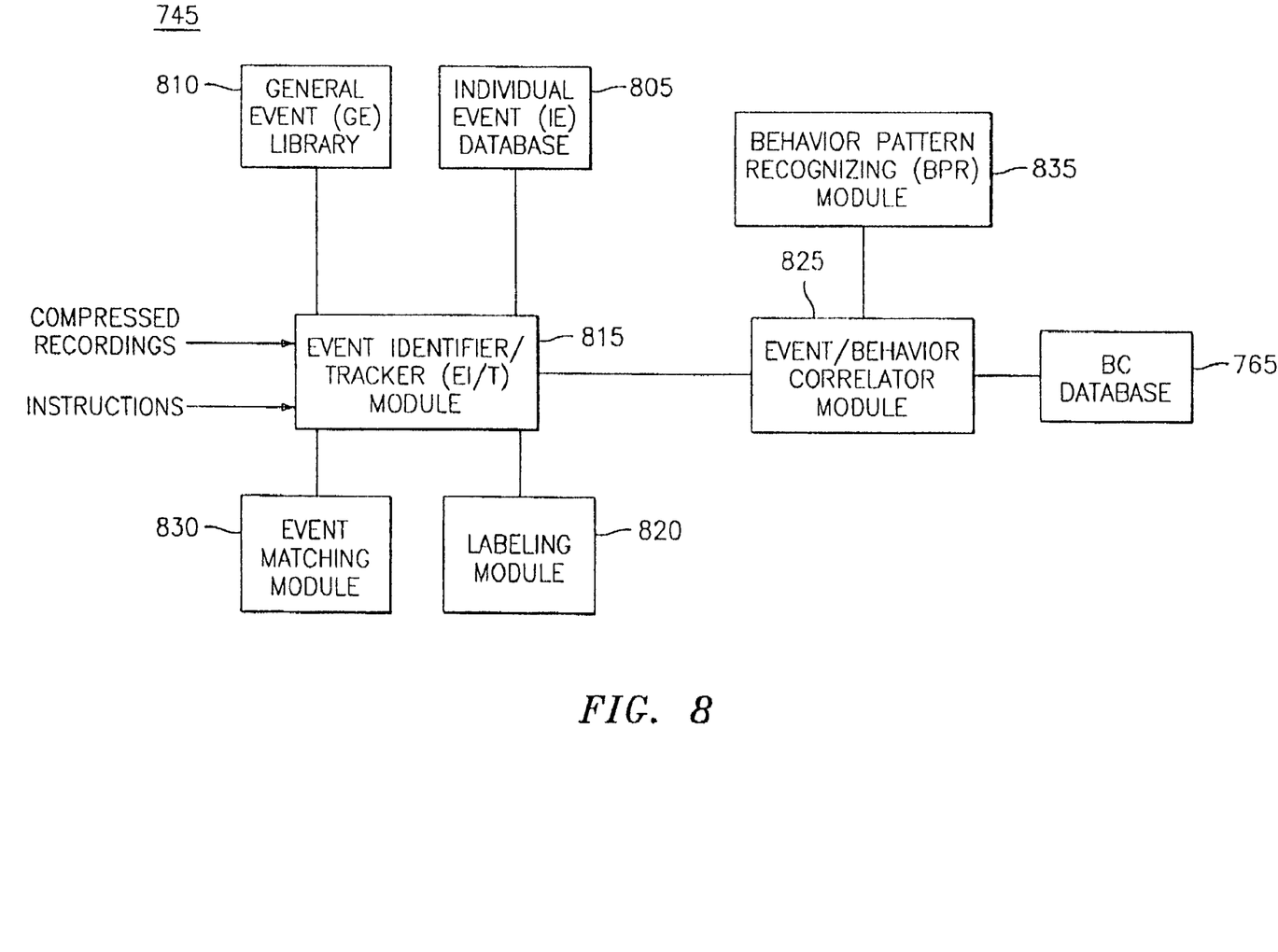
FIG. 8 is a block diagram of the Situational Analyzer according to the preferred embodiment of the present invention.

With reference to FIG. 8, when event data is entered for an individual, it is stored in an Individual's Event (IE) Database 805 which is linked to the Individual Personal Data Database for that individual. The IE Database 805 is comprised of records, each record storing information relative to an event. A General Event (GE) Library 810 is provided for storing a variety of possible events which might occur. The GE Library 810 is comprised of records, each record storing information relative to an event.

In the inventive system, the SA Module 745 can be provided as an optional unit. In the preferred embodiment, in which the SA Module 745 is provided, a user 110 has the option to deactivate it. The SA Module 745 can be activated by user request or by the system's internal instructions.

When activated, control is passed to the SA module 745 by the control module 710, along with specific instructions. The compressed images to be processed are provided by the File Manager. The compressed recordings are provided as a steady stream or as a finite segment.

The modules of the SA Module 745 will now be discussed in detail. An Event Identifier/Tracker (EI/T) Module 815 receives the compressed recordings for detecting and identifying the occurrence of an event. Methods for detection of the occurrence of an event can include object recognition, tracking objects, tracking the individual for location relative to objects, tracking the time of an occurrence or expected occurrence in the individual's schedule and tracking the time of a change in the individual's condition. The Event Identifier/Tracker Module 815 compares the recognized object or event to records stored in the Individual's Event Database 805 and the General Event Library 810. Events which were recognized, but could not be identified, are transmitted to a Labeling Module 820 for labeling the event, creating a record and entering it into the appropriate Event Database or Library. The event can be transmitted to the Labeling Module 820 in many forms such as images, compressed images or codes. The Labeling Module 820 can be an automatic intelligent system or a person for recognizing and identifying the event.

Multiple occurrences of a behavior within a selected time interval surrounding an event may indicate a cause and effect relationship. Likewise, the occurrence of an event within a selected time interval surrounding the performance of a behavior indicates a correlation between the event and the behavior. An Event/Behavior Correlator Module (E/BC) Module 825 recognizes when a correlation between an event and a behavior exists and updates the related event data list field 335 of the behavior record stored in the BC Database 765 for events correlated to the behavior. Event data stored in field 335 includes the code associated with the correlated event, the number of recorded occurrences of each event and the time of the occurrence relative to the behavior.

The SA 745 may be activated for the case in which a user has requested notification of occurrences of a specified event. Each event recognized is compared by an Event Matching Module 830 to the specific requested event, in order to find a match. When a match is found, control will return to the Behavior Coder Module 740 for examining a specified time interval preceding and/or following each occurrence of a matching event for recognizing behaviors within that time interval. The Behavior Matching Module 755 will match the recognized behaviors to stored behaviors in the Behavior Code Database 765. The recognition and identification of a behavior within the specified time interval indicates that there may be a cause and effect relationship between the specific event and the matched behavior code. Control returns to the Event/Behavior Correlation (E/BC) Module 825 of the SA 745 for updating the related event data list field 335 of the matching behavior code. For the case in which the specific requested event was not recognized in the images provided, control is returned to the Report Generator 770 for returning a message to the user interface 116.

The SA 745 may further be activated for the case in which the system or user have requested identification of all recognized events occurring within a segment of compressed images provided. The user may have requested that the system find a correlation between a specific behavior or behavior pattern and any events which have occurred within a specific time interval prior to or following the specified behavior. A system request is generated when the system recognizes that the related event field 335, primary explanation field 320, or the related explanation field 330 for a certain behavior code are still blank. The system tries to generate an explanation for the behavior associated with the behavior code by examining the associated compressed images of each occurrence of the behavior stored in the behavior code database. A specified time interval prior to and/or following each instance of the behavior is searched for the occurrence of any events. The system correlates any related events to the behavior.

The E/BC Module 825 updates the BC Database 765 by recording each event identified in the related events field 335 of the behavior code associated with the behavior being analyzed. Alternatively, the E/BC Module 825 uses intelligent processing to enter only the events which are likely to be related. The E/BC Module 825 looks for a pattern of events and makes a determination as to which events are most likely related to the behavior. The results are then sent to the Report Generator 770.

A Behavior Pattern Recognizing (BPR) Module 830 examines the Individual BC Database for patterns of behavior for the purpose of grouping behaviors together which typically occur approximate one another. Upon determining that a group of behaviors are related, the BPR Module 830 examines the related event field 335 of each of the behaviors within the group. The BPR Module 830 determines if there are common related events amongst the group indicating that an event may be the cause of a number of related behaviors. The results are then sent to the Report Generator 770.

The SA 745 further functions to recognize when an event occurs which presents potential danger to the individual. Examples of dangerous events include exposure to a severe allergen, ingestion of a choking hazard, the individual makes contact with a sharp object or a poisonous substance, the individual approaches an electric or fire hazard, a serious medical condition is sensed by a monitor, etc. . . . The event records in the Individual Event Database and the General Event Library include a field for indicating which events pose a danger. Upon detection of a dangerous event, the results are sent to the Report Generator for transmitting an alert to the user or caretaker of the individual. Furthermore, control is passed to the Behavior Coder Module for determining if a behavior has occurred which indicates that the individual is in trouble. Trouble behaviors being searched for could include typical choking gestures or sounds, inactivity, seizure, screaming, severe crying, etc. . . .

Subscribers can access the subscriber, behavior code and image data bases to look up information. Subscribers may be allowed to add information to behavior records such as adding to the lists for possible causes, explanations and recommendations. Various levels of access to information can be assigned to subscribers and public users.

In the preferred embodiment the system provides the user interface with the software necessary for allowing the user to exchange information with the AP via the Web *Screens. Via the Web screens the user can browse and search the general databases for specific information. The User Query Module 720 handles the user requests, accesses the appropriate database, retrieves the information requested and provides the information to the Web Interface Server for returning the requested information to the user interface. In addition the users of the system can communicate with other users and experts. Furthermore, users and experts can communicate with one another interactively and in group formats such as chat rooms.

While the invention has been described with respect to the preferred embodiment, it should be understood that the invention is not limited to this embodiment, but, on the contrary, the invention is intended to cover all modifications, equivalents, and alternatives falling within the spirit and scope of the invention as defined by the appended claims.

The invention claimed is:

1. A system for interpreting nonverbal communicative behavior of an individual, the system comprising:
   means for recording a behavior performed by the individual;
   a user interface in communication with the recording means for receiving recordings; and
   an Analysis Provider Server in communication with the user interface, said Analysis Provider Server receiving a recording of a behavior in the form of a file of a series of frames;
   said Analysis Provider Server comprising;
   means for assigning a recorded behavior code to the recorded behavior, said means for assigning including a Digitize and Sample Module for sampling the frames of the received recording at regular intervals and forming the sampled frames into a digital compressed formatted File of Sampled Frames with each sampled frame having a time stamp indicative of the relative time it was recorded, and a Behavior Coder (BC) Module for recognizing behavior units which comprise the behavior, assigning a behavior unit code to each behavior unit, and combining the behavior unit codes to form a recorded behavior code;

a Behavior Code Database for storing known behavior codes associated with known behaviors, each known behavior code having an associated explanation associated thereto and including the behavior unit codes; and means for comparing the recorded behavior code with the known behavior codes in the Behavior Code Database and retrieving the explanation associated with each of the known behavior codes which match the recorded behavior code, said means for comparing including a Behavior Code Matching (BCM) Module for searching the Behavior Code Database for behavior codes having behavior units having property units matching the property units of the observed behavior code;

wherein the behavior units comprise gesture units and sound units, the behavior unit codes comprise gesture unit codes, sound unit codes, and property unit codes, and the property unit codes of a gesture unit code comprise a body part unit code, a movement type unit code, a body position unit code and a duration unit code, and the behavior unit codes comprising the recorded behavior code are prioritized according to one of: chronological order, frequency of occurrence in database and degree of dominance;

and wherein a user enters, via the user interface, a requested series of behavior codes, and the Analysis Provider Server comprises a Behavior Series Matching (BCM) Module for determining when the individual performs a series of behaviors which correspond to the requested series of behavior codes.

2. The system according to claim 1, wherein the Digitize and Sample Module is in communication with a Noise Elimination Module for eliminating from the sampled frames recorded activity which is not meaningful to behaviors of the individual.

3. The system according to claim 1, wherein the BC Module is in communication with a Synchronizer Module for synchronizing the gesture unit codes and the sound unit codes to form the recorded behavior code.

4. The system according to claim 1, wherein the BC Module is in communication with a Behavior Begin/End Detector Module for determining the end of the recorded behavior and the beginning of a subsequent recorded behavior.

5. The system according to claim 1, wherein the BC Module concatenates the behavior unit codes in chronological order, with each behavior unit code indicating when the associated behavior unit occurred simultaneously with the behavior unit associated with the previous behavior unit code.

6. The system according to claim 1, wherein the property unit codes of a sound gesture code comprise a sound description unit code, a sound intensity unit code, a sound pitch unit code and a duration period code.

7. The system according to claim 1, wherein the Behavior Code Database is searched according to the priority of the behavior unit codes and the property unit codes.

8. The system according to claim 1, wherein the means for comparing the recorded behavior code with the known behavior codes stored in the database synchronizes the comparison of the gesture unit codes and the sound unit codes of the recorded behavior code to the gesture unit codes and the sound unit codes of the stored behavior codes.

9. The system according to claim 1, wherein the Analysis Provider Server further comprises an Individual Personal Data database for storing data about the individual, the data comprising identification, age, body measurements and voice characteristics.

10. The system according to claim 9, wherein the Digitize and Sample Module is in communication with a Scaling Module for applying a scaling factor selected according to the data stored in the Individual Personal Data database to the sampled frames of the digital compressed file for providing a standardized version of the sampled frames to the means for assigning a recorded behavior code to the recorded behavior.

11. The system according to claim 1, wherein the Analysis Provider Server further comprises a Query Module for processing user requests to enter and access data stored in the AP Server.

12. The system according to claim 11, wherein the Analysis Provider Server further comprises a Report Generator Module for transmitting messages, results from submitted requests and alerts to the user interface.

13. The system according to claim 1, wherein the AP Server provides the user interface with interactive web pages to enable a user
  to submit one of a live stream of recordings and a selected recorded segments;
  and to enable the user to request that the AP Server recognize at least one of a specific behavior, a specific series of behaviors, a specific event, all behaviors and all repeated behavior pattern.

14. The system according to claim 13, wherein the AP server enables the user to request that the AP Server correlate at least one of a behavior to a specified event, an event to a specified behavior, an event to a specified series of behaviors, and correlation of events to all recognized behaviors.

15. The system according to claim 13, wherein the user specifies a behavior and a series of behaviors by entering, at a Web Page provided, one of the behavior codes for each behavior, the identification number for each behavior and behavior units comprising the behavior.

16. The system according to claim 1, wherein the Analysis Provider Server further comprises a Web Server for receiving data from and transmitting data to the user interface.

17. The system according to claim 16, wherein the Analysis Provider Server further comprises a Subscriber Database for storing data relative to the users of the system comprising an identification number, personal data and financial data.

18. The system according to claim 17, wherein the Behavior Code Database comprises a record for each behavior code, each record comprising a field for storing:
  the behavior code; an Identification Number for the behavior code; a link to the file of the received recording; a link to the File of the Sampled Frames; a primary explanation for the behavior code; a link to a list of similar behavior codes; a link to a list of related explanations for the behavior code with dates of entry and identification numbers for the submitting users; recommendations related to the behavior code with dates of entry and identification numbers for the submitting users; an identification number for the user who first submitted the behavior code; an identification number for the individual; and an indicator that the behavior code indicates that the individual is in danger.

19. The system according to claim 18, wherein the Analysis Provider Server further comprises an Individual Behavior Codes Database for storing records for at least one of behavior codes or series of behavior codes performed by the individual, wherein each record comprises a field for storing:
the behavior code; a key number for the behavior code; a link to the file of the received recording; a link to the File of the Sampled Frames; a primary explanation for the behavior code; a link to a list of similar behavior codes; a link to a list of related explanations for the behavior code; recommendations related to the behavior code; and an indicator that the behavior code indicates that the individual is in danger.

20. The system according to claim 19 wherein each record at least one of the Behavior Code Database and the Individual Behavior Code Database further comprises a field for storing a link to event data, wherein the event data comprises an event code for each event which has been correlated with the behavior code, the time of the occurrence of each correlated event relative to the occurrence of the behavior associated with the behavior code, and the number of occurrences of each correlated event.

21. The system according to claim 19, wherein the Analysis Provider Server further comprises an Individual Event Database for storing events relating to the schedule, environment and condition of the individual, each event having an event code and a danger indicator which indicates if the event poses a danger to the individual.

22. The system according to claim 21, wherein the user enters events into the Individual Event Database, at a Web Page provided, by one of: entering descriptions of each event; viewing the recording in a view window on a Web Page, selecting an object displayed in the view window and identifying the object; and viewing the recording in a view window on a Web Page and entering the event which occurred at the time shown in the view window.

23. The system according to claim 21, wherein the Analysis Provider Server further comprises a Situational Analyzer (SA) Module for correlating events to recorded and stored behavior codes and series of behavior codes;
wherein the events influence the behavior of the individual and comprise at least one of: a) a presence of an object, b) movement of an object, c) movement of the individual relative to an object d) an occurrence in the schedule of the individual, e) an occurrence expected to take place in the schedule of the individual, or f) a detected change in the condition of the individual.

24. The system according to claim 23, wherein the SA Module further comprises a Behavior Pattern Recognizing (BPR) Module, wherein said BPR Module recognizes the repetitive occurrences of series of behavior codes for establishing behavior patterns and recognizes the occurrence of a behavior pattern performed by the individual.

25. The system according to claim 23, wherein the Situational Analyzer Module comprises:
a General Event Database;
an Event Identifier/Tracker (EI/T) Module for tracking objects and recognizing the occurrence of events in the File of Sampled Frames; and
an Event/Behavior Correlator (E/BC) Module for correlating recognized events with behaviors recorded in the File of Sampled Frames.

26. The system according to claim 25, wherein the EI/T Module recognizes objects in the File of Sampled Frames and identifies the objects by looking them up in the Individual Event Database and the General Event Database.

27. The system according to claim 25, wherein the SA Module further comprises a Labeling Module for identifying events; and
wherein the EI/T Module queries the Labeling Module when a recognized event is not identified, and upon receiving a successful identification of the event from the Labeling Module, the EI/T adds the event into at least one of the Individual Event Database or General Event Database.

28. The system according to claim 25, wherein the E/BC Module correlates recognized events to the behavior recorded in the File of Sampled Frames by determining when a recognized event occurs within a selected time interval preceding and following the performance of the behavior; and
updates the associated event data of the behavior code associated with the performed behavior in at least one of the Behavior Code Database and the Individual Behavior Code Database.

29. The system according to claim 25, wherein the Individual Event Database and the General Event Database include a field for each event which indicates when the occurrence of the event poses a threat to the individual;
and wherein the SA Module causes an alert to be transmitted to a caretaker of the individual upon recognition of the occurrence of danger posing event.

* * * * *